(12) United States Patent
Anderson

(10) Patent No.: US 11,969,170 B2
(45) Date of Patent: Apr. 30, 2024

(54) DEVICES AND METHODS FOR THE TREATMENT OF EPISTAXIS AND FOR AESTHETIC MEDICINE

(71) Applicant: Asher Anderson, Golden Valley, MN (US)

(72) Inventor: Asher Anderson, Golden Valley, MN (US)

( * ) Notice: Subject to any disclaimer, the term of this patent is extended or adjusted under 35 U.S.C. 154(b) by 166 days.

(21) Appl. No.: 17/712,131

(22) Filed: Apr. 2, 2022

(65) Prior Publication Data

US 2022/0313266 A1 Oct. 6, 2022

Related U.S. Application Data

(60) Provisional application No. 63/171,007, filed on Apr. 5, 2021.

(51) Int. Cl.
*A61B 17/12* (2006.01)
*A61B 17/00* (2006.01)
*A61B 17/24* (2006.01)

(52) U.S. Cl.
CPC ........ *A61B 17/12009* (2013.01); *A61B 17/24* (2013.01); *A61B 2017/00557* (2013.01); *A61B 2017/00876* (2013.01); *A61B 2017/12004* (2013.01)

(58) Field of Classification Search
CPC ... A61B 17/12; A61B 17/12009; A61B 17/24; A61B 2017/00557; A61B 2017/00876; A61B 2017/12004; A61B 2017/08021
See application file for complete search history.

(56) References Cited

U.S. PATENT DOCUMENTS

2016/0324526 A1* 11/2016 Ibarra .................... A61B 17/24
2016/0367276 A1* 12/2016 Moloney ................ A61F 13/38

* cited by examiner

*Primary Examiner* — Jocelin C Tanner
(74) *Attorney, Agent, or Firm* — Wagenknecht IP Law Group PC

(57) ABSTRACT

Devices and methods for restricting the flow of blood through tissue of a human face, which include an insertion body having a magnetized face that is configured for insertion into a human mouth; and an external body having an oppositely magnetized face configured for attraction to the magnetized face of the insertion body, where the insertion body and external body have a sufficiently attractive magnetic force that when placed against opposing surfaces of the tissue of the face, the tissue is sufficiently compressed to restrict the flow of blood through the tissue.

11 Claims, 6 Drawing Sheets

DEVICES AND METHODS FOR THE TREATMENT OF EPISTAXIS AND FOR AESTHETIC MEDICINE

CROSS REFERENCE TO RELATED APPLICATIONS

This application claims benefit of priority to U.S. provisional patent application No. 63/171,007, filed Apr. 5, 2021, the entire content of which is herein incorporated by reference in its entirety.

FIELD OF THE INVENTION

The invention relates to devices and methods for restricting the flow of blood through the vasculature of the human face and its applications for use in medical treatments including epistaxis and aesthetic medicine.

BACKGROUND OF THE INVENTION

Currently, there lacks an efficient way to treat epistaxis (i.e. nosebleeds). Conventionally, products such as nose plugs, nasal tampons, nasal gels, nasal clips, or even just tissue packed into the nostrils of an individual suffering from a nosebleed have been used. However, nose plugs, nasal tampons, and tissue can cause the bleeding to worsen because they irritate the vessels further through friction and often do not provide enough pressure to stop the bleeding. Nasal gels release calcium ions that act as absorbers to blood, but the gel can be easily overflown with strong nosebleeds and can also irritate the individual's nostrils. Nasal clips only keep the nostrils closed and do not address the vasculature causing the bleeding. Additionally, nasal clips can easily slip off of an individual's nose since they are not usually designed to accommodate various nose sizes and shapes. It would, therefore, be desirable to provide an improved device and method for treating epistaxis.

SUMMARY OF THE INVENTION

The invention addresses the above-described deficiencies in the treatment of epistaxis and provides related benefits, which also extend to areas of aesthetic medicine. In particular, the invention selectively targets blood vessels in the human face that lead to areas where bleeding is occurring and restricts the flow of blood through the vessels, thereby stopping or slowing the bleeding. The above is achieved in some embodiments by way of a device for restricting the flow of blood through tissue of a human face, which includes an insertion body having a magnetized face that is configured for insertion into a human mouth, the insertion body also having a cutaway positioned in a mid-region between two opposite ends of the insertion body, the cutaway sized to receive a labial frenum of the human mouth; and an external body having an oppositely magnetized face configured for attraction to the magnetized face of the insertion body, the insertion body and external body having a sufficiently attractive magnetic force that when placed against opposing surfaces of tissue of the face, the tissue is sufficiently compressed to restrict the normal flow of blood through the tissue positioned between the insertion and external bodies.

In some embodiments the device is for the treatment of epistaxis and in some embodiments the cutaway extends more than 50% into the insertion body The above referenced device can also be integrated into a kit. Accordingly, a kit for restricting the flow of blood in a human face is provided, which includes a plurality of the devices, where one of the devices has a greater attractive magnetic force than another device. As such, the kit can be used across different age groups and sensitivities.

Relatedly, also provided is a method of treating epistaxis by restricting the flow of blood to a nasal region of a subject suffering from epistaxis. An exemplary method includes providing the above-described device; and positioning the insertion body inside the mouth of the subject so that the labial frenum is received into the cutaway and the magnetized face abuts the upper lip region, and positioning the external body outside of the mouth and opposite the insertion body so that the vasculature of the face is compressed between the insertion and external bodies, thereby restricting the flow of blood flow to the nasal region of the subject. In some embodiments, the method can also include expanding the insertion body after positioning the insertion and external bodies.

In a related aspect, the invention also provides a method of restricting the flow of blood flow through tissue of a human face, which includes providing a device having an insertion body with a magnetized face and an external body with an oppositely magnetized face, where the insertion and external bodies have a sufficiently attractive magnetic force to one another that when the magnetized faces abut opposing surfaces of the tissue, the bodies compress the tissue in an amount that restricts the flow of blood through the vasculature of the face that is positioned between the insertion and external bodies; and positioning the insertion body inside the mouth and the external body outside of the mouth so that the magnetized faces abut opposing surfaces of the mouth, thereby compressing the vasculature of the face to restrict the normal flow of blood.

In some embodiments, the insertion body is positioned against an inner surface of the upper lip and the external body is positioned on an outer, opposing surface of the upper lip, thereby reducing the flow of blood to a nasal region of the face.

In some embodiments the insertion body has an expandable cavity, and the method also includes expanding the cavity after both surfaces abut the opposing surfaces of the mouth.

In some embodiments the insertion body has a cutaway configured to receive a labial frenum of the human mouth, and the method also includes positioning the insertion body so that the labial frenum is received by the cutaway.

In some embodiments the device is used for the treatment of epistaxis, and where the device is placed on opposing surfaces of an upper lip of a subject suffering from epistaxis.

BRIEF DESCRIPTION OF THE DRAWINGS

Embodiments of the present disclosure and their advantages are best understood by referring to the detailed description that follows. It should be appreciated that like reference numerals are used to identify like elements illustrated in one or more of the figures.

DESCRIPTION OF PREFERRED EMBODIMENTS

Provided are devices and methods for selectively restricting the normal flow of blood in regions of the human face, which are useful in the treatment of medical conditions or injury where the targeted restriction of blood flow is beneficial. In particular, the normal flow of blood can be stopped or slowed so that the volume of blood passing through one or more blood vessels is substantially decreased, such as decreased by 20% or more, 40% or more, 50% or more, 60% or more, 65% or more, 70% or more, 75% or more, 80% or more, 85% or more, 90% or more, 95% or more, or 99% or more. By stopping or slowing the flow of blood to a region where blood loss is occurring, the device not only reduces the total volume of blood loss but also the rate at which blood is lost, which can accelerate the body's natural clotting defense. The above is achieved by the targeted compression of blood vessels using a device that is easy to apply and with very little risk of injury to the subject. The invention will now be described with reference to the drawings, which are shown for purposes of illustrating embodiments of the present invention only and not for the purposes of limiting the same.

Figure 1:
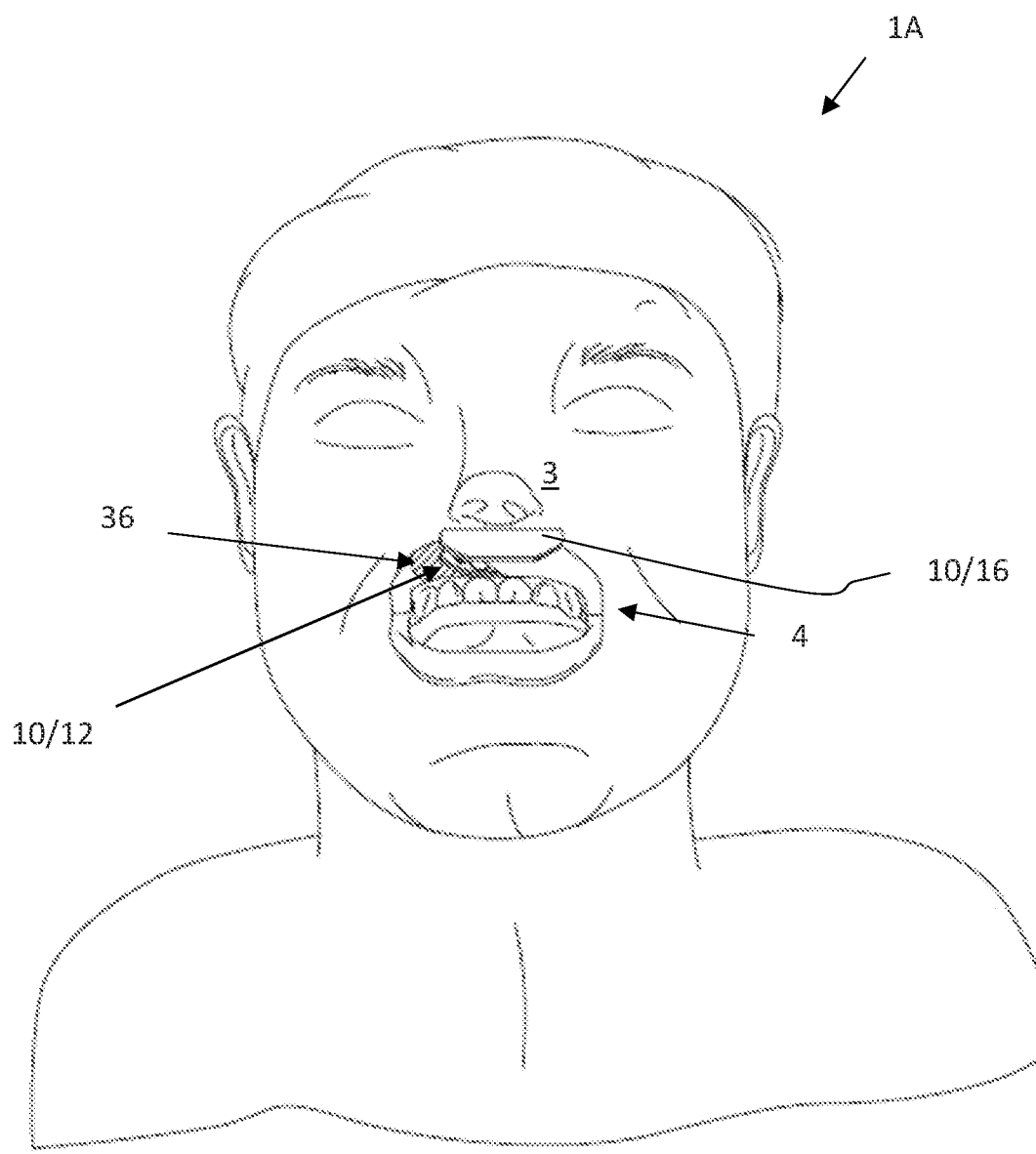
FIG. 1 is a partial cutaway view of a subject undergoing treatment for epistaxis.
Figure 2:
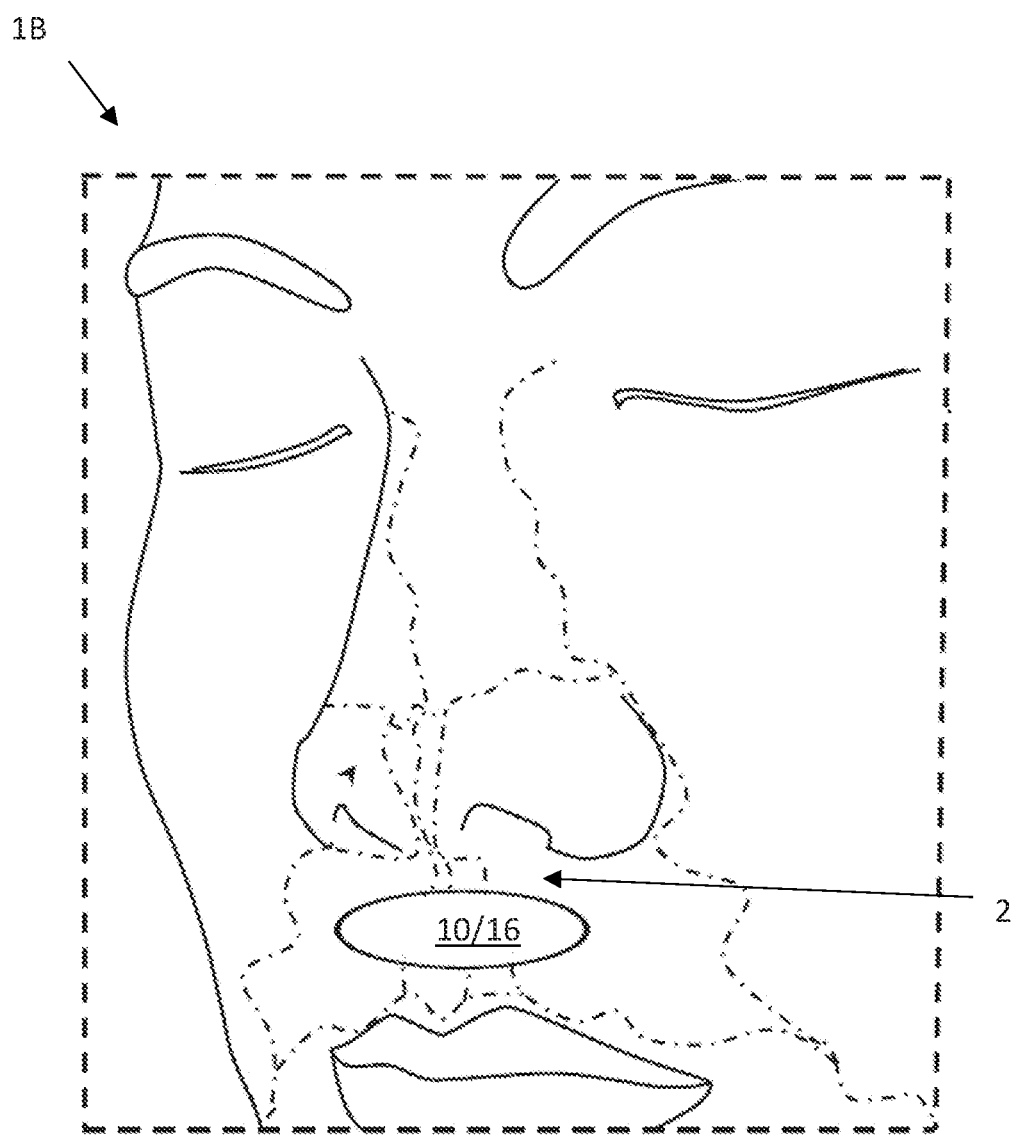
FIG. 2 depicts a technical approach of restricting the flow of blood to the nasal region by selectively compressing blood vessels that access the nasal region through the upper lip.

Beginning at FIG. 1 and FIG. 2, an exemplary method of restricting the flow of blood through tissue of a human face is provided. In particular, the subjects 1A. 1B exemplified in FIGS. 1 and 2 suffer from epistaxis. Nasal hemorrhaging is substantially slowed by producing a pulse pressure against the perioral or angular facial vasculature, thereby creating direct or indirect temporary compression of the blood supply tributaries. That is, by applying intraoral compression against the vasculature of the upper lip 2, blood flowing into the nasal region 3 is restricted, thereby reducing blood loss, and reducing the time needed for the body to perform its clotting defense to treat the epistaxis.

Figure 3:
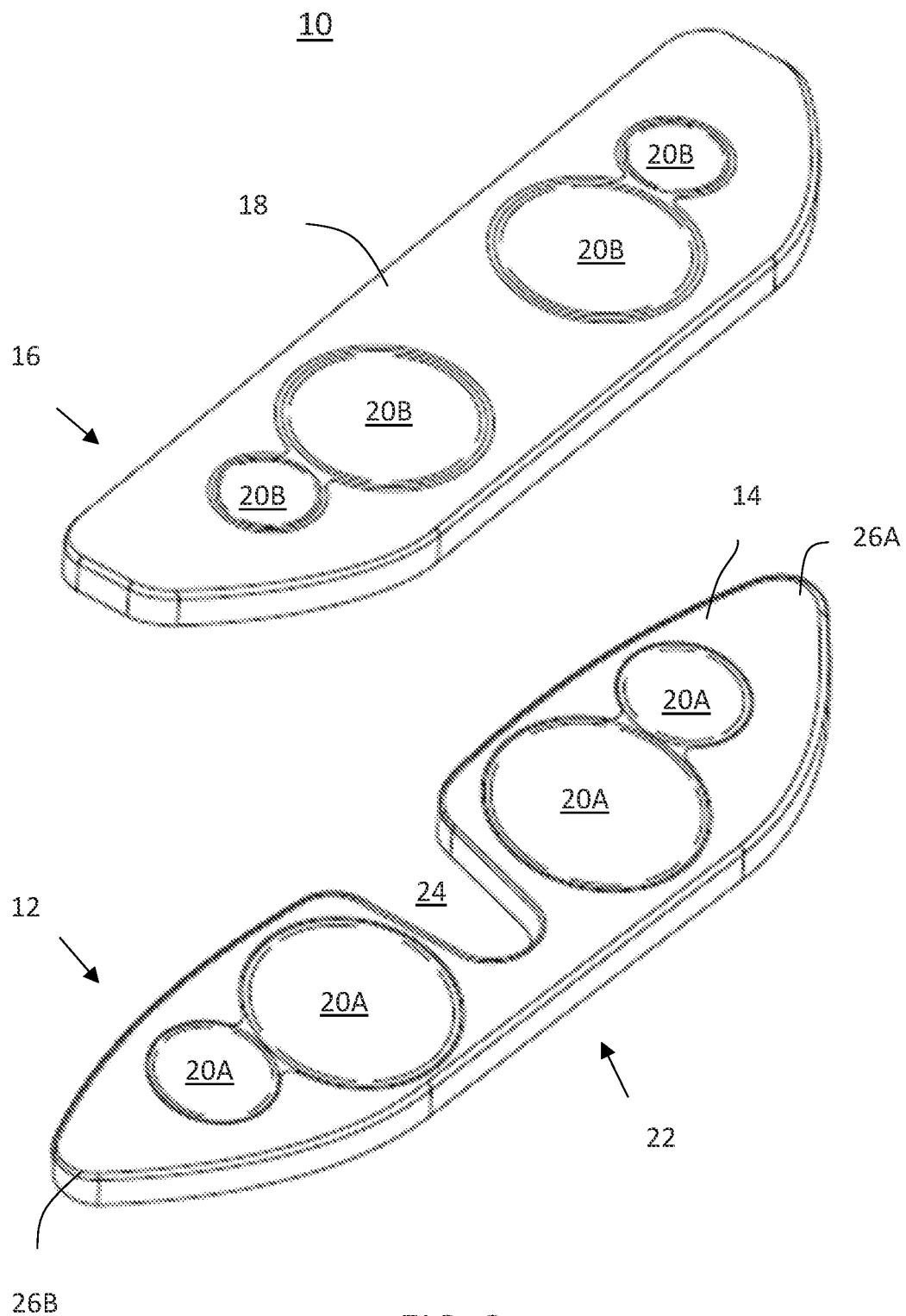
FIG. 3 depicts an exemplary device for restricting the flow of blood through tissue of a human face.

Moving on now to FIG. 3, restricting blood flow is performed in some embodiments by way of a device 10, which includes an insertion body 12 having a magnetized face 14, which is configured for insertion into the mouth 4 of the subject 1A, 1B (see FIGS. 1A, 1B), and an external body 16 having an oppositely magnetized face 18 configured for attraction to the magnetized face 14 of the insertion body 12. The insertion body 12 and external body 16 have a sufficiently attractive magnetic force that when placed against opposing surfaces of the tissue of the mouth 4 and facing one another, the blood vessels within the tissue are compressed, which substantially slows the passage of blood.

The insertion body 12 and external body 16 can be made magnetic by manufacturing the bodies 12, 16 with integrated magnets 20A, 20B. That is, the insertion body 12 and external body 16 can be formed from nonmagnetic materials such as polymer plastic, silicon and the like and made to be magnetic by the addition of magnets 20A, 20B. To ensure magnetic attraction between one another, magnets 20A, 20B within the insertion body 12 and the external body 16 are preferably of opposite polarity. That is, in some embodiments the magnetized face 14 of the insertion body 12 displays a magnetic north pole while the oppositely magnetized face 18 of the external body 16 displays a magnetic south pole. Naturally, in other embodiments, the magnetized face 14 of the insertion body 12 displays a magnetic south pole while the oppositely magnetized face 18 of the external body 16 displays a magnetic north pole. Though less preferred, in other embodiments, either the magnetized face 14 of the insertion body 12 or the oppositely magnetized face 18 of the external body 16 includes a magnet 20A, 20B and the other includes a magnetizable material such as iron that is made magnetic when placed in the magnetic field of the other, thereby forming two magnetized faces 14, 18 that attract one another.

In view of the above, the skilled artisan will appreciate that on the one hand, the attractive magnetic force between the magnetized faces 14, 18 should be of a sufficient strength to compress blood vessels positioned between the insertion body 12 and the external body 16, but on the other hand the attractive magnetic force shouldn't be so strong that the subject 1A, 1B is bruised, unless bruising is acceptable under the particular situation (e.g. emergency surgery). As such, the device 10 includes different embodiments that vary in their attractive magnetic force. Furthermore, devices 10 of different attractive magnetic forces can be combined in a kit so that the different devices 10 can be chosen according to the needs of the subject 1A, 1B, such as the subject's age, size, sensitivity, and risk of continued bleeding.

In some embodiments, varying the attractive magnetic force is accomplished by increasing the size of magnets 20A, 20B within the insertion body 12 and/or external body 16, where larger magnetics 20A, 20B tend to yield a higher attractive magnetic force than smaller magnets 20A, 20B of a same material. In other embodiments, the attractive magnetic force is modulated by choice of magnetic material, such as but not limited to rare earth magnets, neodymium magnets, samarium cobalt magnets, alnico magnets, and ceramic or ferrite magnets. In still other embodiments, the attractive magnetic force is adjusted by recessing magnets 20A, 20B within the insertion body 12 and/or external body 16 to different depths and applying a coating over the magnetized face 14, 18 to reduce its attractive magnetic force. In still other embodiments, the number of magnets 20A, 20B vary, where a greater number of magnets 20A, 20B would tend to yield a greater attractive magnetic force compared to a fewer number of magnets 20A, 20B. Still another approach is depicted in FIG. 3, where both the number and size of magnets 20A, 20B is varied to generate the desired attractive magnetic force. Preferably, each body 14, 16 includes 4 magnets 20A, 20B, namely, two larger magnets 20A, 20B positioned between and two smaller magnets 20A, 20B. This configuration directs the majority of the attractive magnetic force near the mid-region 22 of the device 10, which as shown in more detail in FIG. 2 overlaps the blood vessels leading towards the nose region 3 when applied to the upper lip 2, and a lesser attractive magnetic force, which tends to make removal of the device 10 easier and yet helps keep the bodies 12, 16 aligned generally parallel to one another during treatment.

Also shown in FIG. 3 is a cutaway 24 positioned at the mid-region 22 of the insertion body 12 and thus between two opposite ends 26A, 26B. Preferably, the cutaway 24 extends more that 50% into the insertion body 12, and more preferably about 60-80% into the insertion body 12. As shown more clearly when combining FIG. 1 and FIG. 3, the cutaway 24 is sized to receive the subject's labial frenum, which permits the insertion body 12 to be positioned higher along the upper lip 2 region of the subject 1A, 1B compared to a configuration without a cutaway 24. This higher positioning is significant in that it improves intraoral compression against the blood vessels because it overcomes the natural blocking position of the labial frenum.

As will be described in more detail below with reference to FIG. 5, in some embodiments, the insertion body 12 also includes an expandable cavity 28, which when expanded such as by pumping air or liquid into the cavity 28, presses against the inner surface 30 of the mouth 4 to directly or indirectly compress blood vessels 32 to restrict the flow of blood 40 through the vasculature.

Figure 4A:
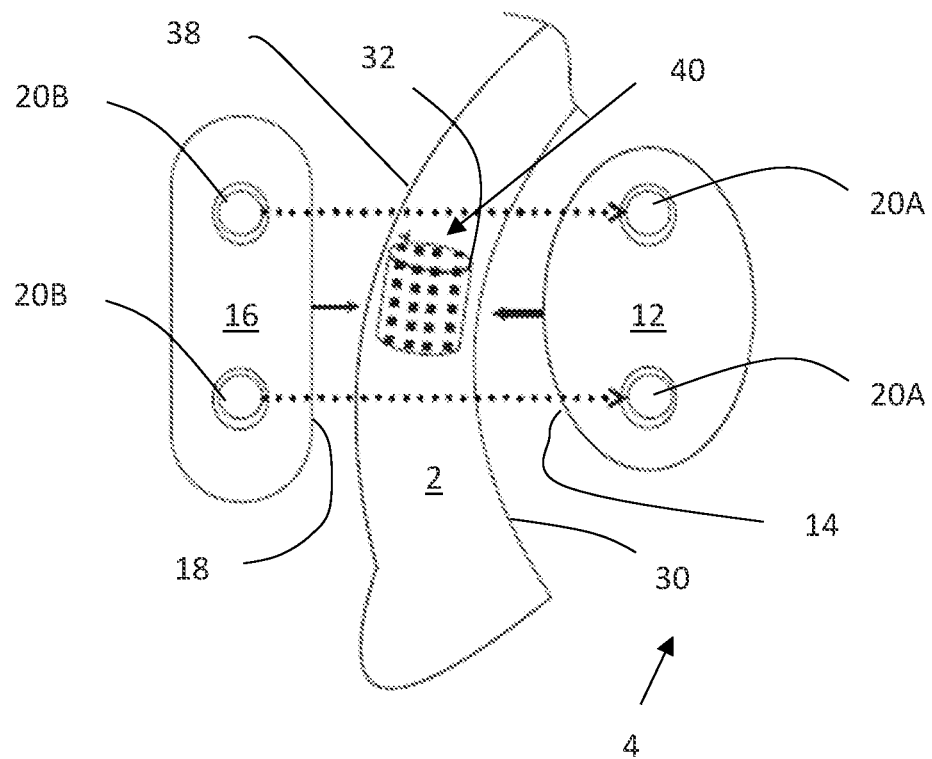
FIGS. 4A-C depict an exemplary method for restricting the flow of blood through tissue of a human face.
Figure 4B:
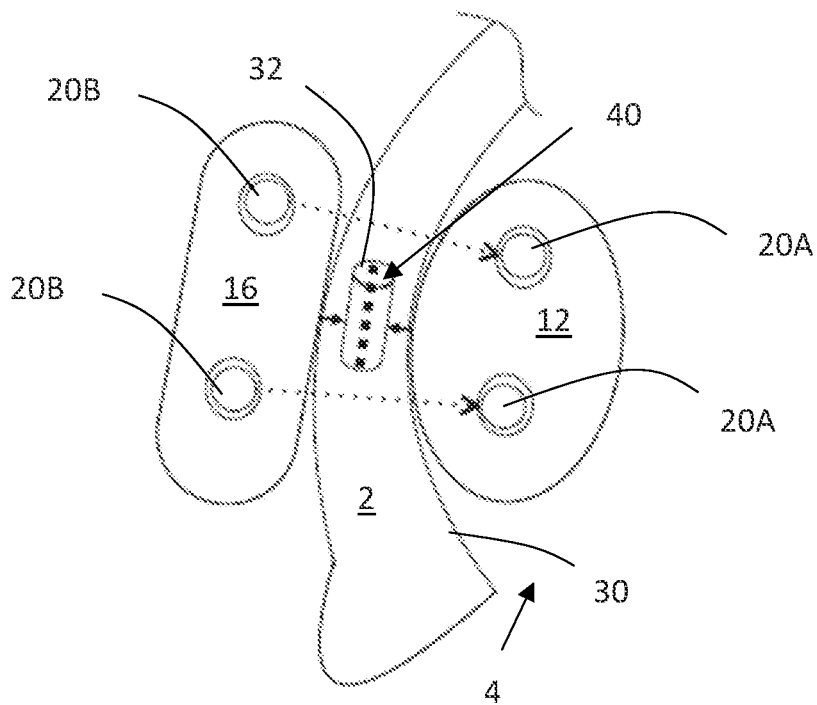
Figure 4C:
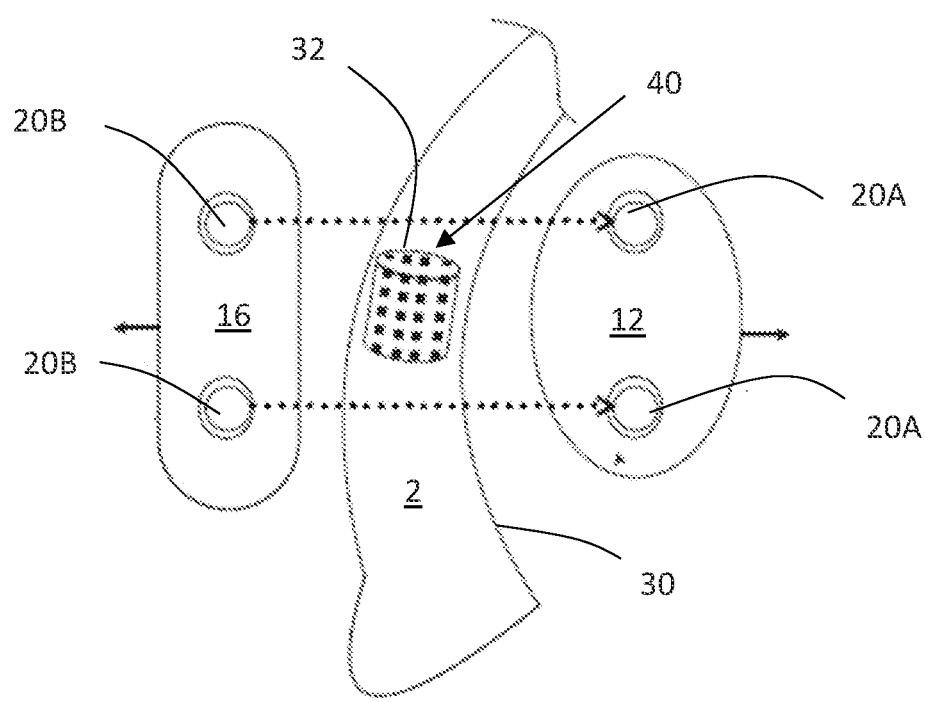

However, moving back to FIGS. 4A-4C an exemplary method of restricting the flow of blood 40 through tissue of a human face is depicted and in particular for the treatment of epistaxis. Beginning at FIG. 4A and with reference to FIG. 1, the insertion body 12 is inserted into the mouth 4. Here the insertion body is positioned between the gum 36 and the inner surface 30 of the upper lip 2 (e.g. about the philtrum) so that the magnetized surface 14 of the insertion body 12 abuts the inner surface 30 of the upper lip 2 area and underneath the nose. Not shown in FIGS. 4A-4C for simplification but with further reference to FIGS. 1 and 3, the insertion body 12 is positioned so that the subject's labial frenum is received into the cutaway 24, which again is positioned at about the mid-region 22 of the insertion body 12, thereby allowing the insertion body 12 to be comfortably positioned high up the upper lip 2 region. While the insertion body 12 is held in place, the external body 16 and in particular the opposing magnetized surface 18 of the external body 16 is brought into contact against the outer surface 38 of the upper lip 2 and beneath the nose (see also FIG. 2). Moving on to FIG. 4B, the magnetic forces attracting the external body 16 to the insertion body 12 compresses the tissue housing blood vessels 32 that lead to the nasal area 3 (see also FIG. 2). As such, the clinician, subject, or helper that is applying the device 10 is no longer required to manually hold the insertion body 12 or the external body 14 as it will remain in place. As shown when comparing FIG. 4A, to FIG. 4B, compression of the upper lip 2 by the insertion and external bodies 12, 16 compresses the blood vessel(s) 32, which substantially slows the flow of blood 40 to the nasal area 3 (see also FIG. 2). The device 10 remains in place until the bleeding is stopped or slowed as desired. Moving on to FIG. 4C, once the results are achieved the external body 16 is pulled away from the outer surface 38 of the lip 2 which permits the lip 2 area to expand back to its normal position, thereby permitting the blood vessel(s) 32 to expand and continue to deliver blood 40 normally.

Figure 5:
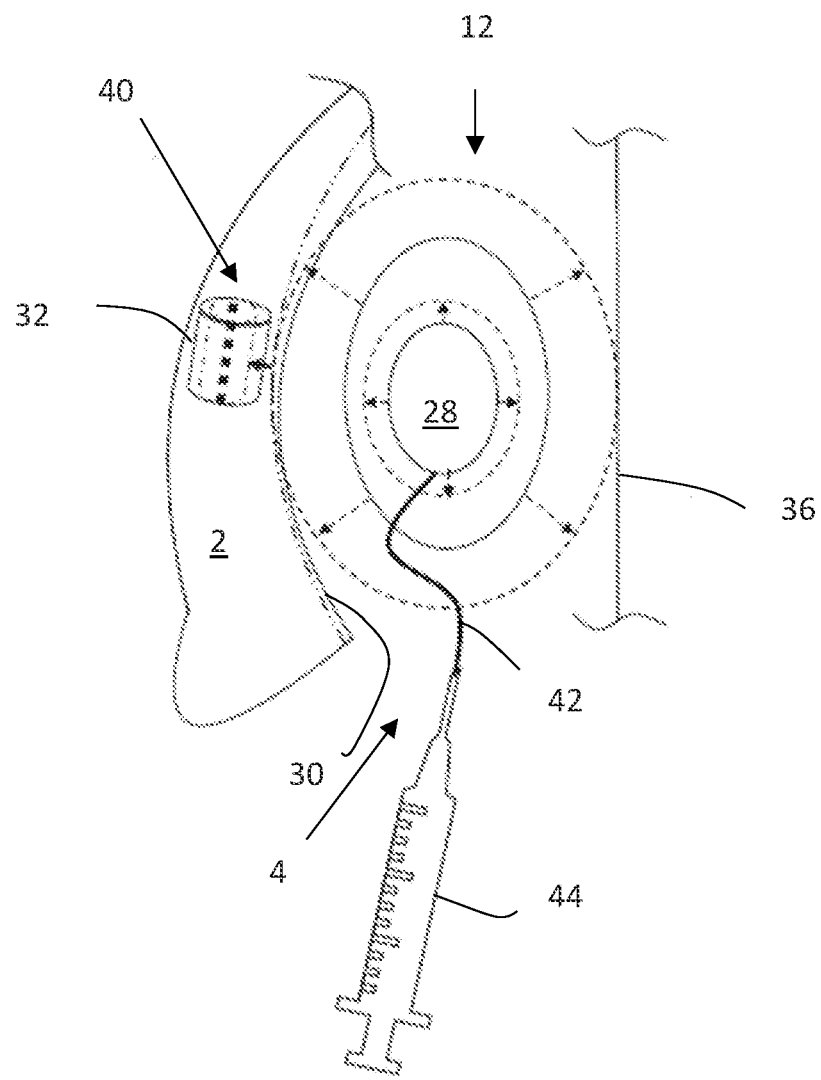
FIG. 5 depicts is another exemplary method for restricting the flow of blood through tissue of a human face.

Concluding with FIG. 5, also provided is a variation of the above, where the insertion body 12 includes an expandable cavity 28, which can be expanded by pumping air or liquid through an access tube 42 into the cavity 28 using a syringe 44 until the tissue is compressed. In particular, enlarging the cavity 28 causes the insertion body 12 to outwardly press against both the gum 36 and upper lip 2, which compresses the tissue of the upper lip 2 and thus causes the internal blood vessel(s) 32 to restrict the flow of blood 40. In some embodiments, this configuration also includes an external body 16 substantially as show in FIG. 3, which tends to anchor the insertion body 12 in place prior to pumping. After the desired results are achieved the air or liquid filling is removed from the cavity 28, thereby allowing the elastic properties of the cavity 28 to return the insertion body 12 to its original position and thus remove the pressure against the blood vessel(s) 32, which permits the blood 40 to flow normally.

Now turning back to FIG. 3, the skilled artisan will appreciate that while the device 10 has primarily been described as a treatment for epistaxis, the device 10 may also be used for other purposes. In particular, the device 10 can used to restrict blood flow while the subject undergoes facial surgery, such as facial reconstructive surgeries or cosmetic surgeries where reduction of blood flow in an area of tissue is desired (e.g., hemostasis).

As a specific exemplary use, the device 10 can be provided for safety during nasolabial fold dermal injections (e.g., fillers or medicaments). Those familiar with the field of aesthetic medicine know that dermal injections of BOTOX and dermal fillers can inadvertently get into the angular artery or vein when injected into the face. This can lead to multiple catastrophic reactions such as anaphylaxis, embolism, tissue necrosis, and/or loss of vision. To prevent such reactions, the diameter of angular artery and vein can be indirectly reduced by using device 100 to compress the lower angular artery and other feeder vessels to the angular vessels, thereby decreasing risk of inadvertent injection.

Another exemplary use may include providing safety for vermillion, or lip, dermal injections (e.g., fillers or medicaments). Dermal injections of BOTOX and dermal fillers can inadvertently get into the labial artery or vein during such injections. This can lead to multiple catastrophic reactions such as anaphylaxis, embolism, tissue necrosis and loss of lip. To prevent such reactions, the diameter of the labial artery and veins can be indirectly reduced by using device 100 to compress the lower angular artery and other feeder vessels to the angular vessels, thereby decreasing risk of inadvertent injection.

Another exemplary use can be to restrict blood flow through areas of tissue during surgeries (e.g., nasal cavity surgeries). For example, during surgery in the nasal cavity, the vessels within the mucosa and tissues can become traumatized and bleed, causing difficult operative field visualization. Thermal cautery carries the risk of a wide field of tissue necrosis, and direct compression can sometimes be unfruitful in controlling hemorrhaging. For this reason, during nasal cavity surgery, placement of device 10 on lip to occlude and decrease pulse pressure to the bleeding vascular nasal cavity bed would be of significant utility. In one or more embodiments, device 10 may deployed only when bleeding is encountered. In other embodiments, device 10 may be used prophylactically just before operation begins in the region of potential bleeding.

Similarly, for facial surgery (e.g., a facelift), the device 10 may be used. During facial surgery, facial vessels can become traumatized and bleed, causing difficult operative field visualization as in the case of a facelift or nasal cosmetic surgery. As previously mentioned, thermal cautery carries the risk of a wide field of tissue necrosis and direct compression can sometimes be unfruitful in controlling bleeding. For this reason, during facial surgery, placement of the device 10 to occlude and decrease pulse pressure to the bleeding facial vessels would be of significant utility.

The skilled artisan will now also appreciate that the invention will be particularly useful in medical facilities such as hospitals or clinics, sports teams for the treatment of athletes injured during sporting events, and by individuals themselves when encountering a risk of excessive bleeding, such as a nosebleed incurred by a subject suffering from hemophilia.

With the above in mind, the disclosure is not intended to limit the present invention to the precise forms or particular fields of use disclosed. It is contemplated that various alternate embodiments and/or modifications to the present invention, whether explicitly described or implied herein, are possible in light of the disclosure. For example, it is contemplated that the various embodiments set forth herein may be combined together and/or separated into additional embodiments where appropriate. Where applicable, the ordering of various steps described herein can be changed, combined into composite steps, and/or separated into sub-steps to provide features described herein.

Although the invention has been described with reference to the above example, it will be understood that modifications and variations are encompassed within the spirit and scope of the invention. Accordingly, the invention is limited only by the following claims.

What is claimed is:

1. A device for restricting flow of blood through tissue of a human face, the device comprising:
   an insertion body comprising a magnetized face that is configured for insertion into a human mouth, the insertion body further comprising a cutaway positioned in a mid-region between two opposite ends of the insertion body, the cutaway sized to receive a labial frenum of the human mouth; and
   an external body comprising an oppositely magnetized face configured for attraction to the magnetized face of the insertion body, the insertion body and external body comprising a sufficiently attractive magnetic force that when placed against opposing surfaces of the tissue of the face, the tissue is sufficiently compressed to restrict blood flow through the tissue.

2. The device of claim 1, wherein the device is for the treatment of epistaxis.

3. The device of claim 1, wherein cutaway extends more than 50% into the insertion body.

4. A kit for restricting flow of blood in a human face, the kit comprising a plurality of the devices of claim 1, wherein one of the devices has a greater attractive magnetic force than another device.

5. A method of treating epistaxis by restricting flow of blood to a nasal region of a subject suffering from epistaxis, the method comprising:
   providing the device of claim 1; and
   positioning the insertion body inside the mouth so that the labial frenum is received into the cutaway and the magnetized face abuts an upper lip region, and positioning the external body outside of the mouth and opposite the internal body so that vasculature of the face is compressed between the insertion and external bodies, thereby restricting the flow of blood to a nasal region of the subject.

6. The method of claim 5, further comprising expanding the insertion body after positioning the insertion and external bodies.

7. A method of restricting flow of blood through tissue of a human face, the method comprising:
   providing a device comprising an internal body comprising a magnetized face and an external body comprising an oppositely magnetized face, wherein the internal and external bodies have a sufficiently attractive magnetic force to one another that when the magnetized faces abut opposing surfaces of the tissue, the bodies compress the tissue in an amount that restricts blood flow through vasculature of the face that is positioned between the internal and external bodies; and
   positioning the internal body inside the mouth and the external body outside of the mouth so that the magnetized faces abut opposing surfaces of the mouth, thereby compressing the vasculature of the face to restrict the blood flow.

8. The method of claim 7, wherein the internal body is positioned against an inner surface of an upper lip and the external body is positioned on an opposing surface of the upper lip, thereby reducing blood flow to a nasal region of the face.

9. The method of claim 7, wherein the internal body further comprises an expandable cavity, the method further comprising expanding the cavity after both surfaces abut the opposing surfaces of the mouth.

10. The method of claim 9, wherein the device is used for the treatment of epistaxis, further wherein the device is placed on opposing surfaces of an upper lip of a subject suffering from epistaxis.

11. The method of claim 7, wherein the internal body comprises a cutaway configured to receive a labial frenum of the human mouth, the method further comprising positioning the internal body so that the labial frenum is received by the cutaway.

* * * * *